United States Patent [19]

Anspach, Jr. et al.

[11] Patent Number: 4,608,965
[45] Date of Patent: Sep. 2, 1986

[54] ENDOSCOPE RETAINER AND TISSUE RETRACTING DEVICE

[76] Inventors: William E. Anspach, Jr., 1349 S. Killian Dr., Lake Park, Fla. 33403; Michael S. Toborowsky, 4774 Apt. A Orleans Ct., W. Palm Beach, Fla. 33406

[21] Appl. No.: 716,542
[22] Filed: Mar. 27, 1985
[51] Int. Cl.⁴ .............................................. A61B 1/00
[52] U.S. Cl. ....................................................... 128/4
[58] Field of Search .......................... 128/4, 5, 6, 7, 20

[56] References Cited
U.S. PATENT DOCUMENTS 1,621,159  3/1927  Evans ........................................ 128/6
4,250,873  2/1981  Bonnet ...................................... 128/7

Primary Examiner—William H. Grieb
Attorney, Agent, or Firm—Jack N. McCarthy

[57] ABSTRACT

An endoscope retainer and tissue retracting device including a soft plastic cylindrical tube for slidably mounting on the probe portion of an endoscope, one end of the tube having a friction fit adjacent the end of the endoscope, a plurality of slits forming flexible strips around the tube adjacent the one end which extend radially outwardly when the ends of the tube are moved together on the probe portion, a screw mechanism fixes the other end of the tube to an endoscope with the strips extending radially outwardly.

10 Claims, 6 Drawing Figures

U.S. Patent
Sep. 2, 1986
4,608,965
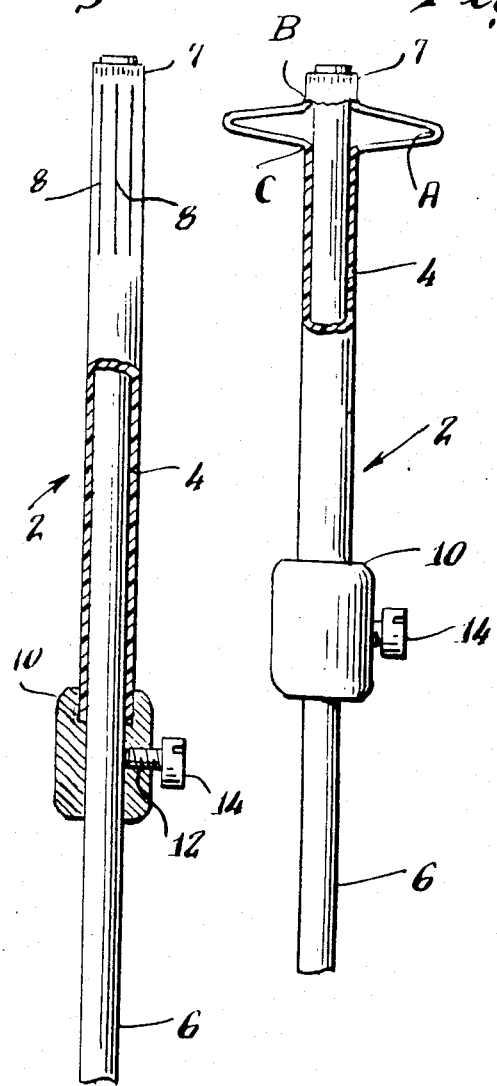
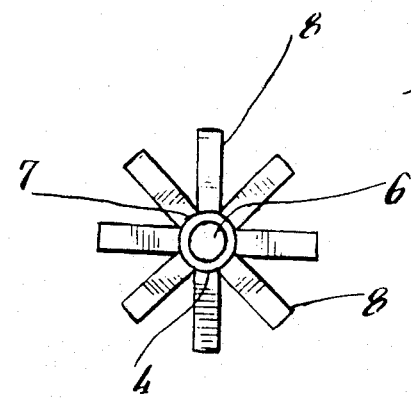
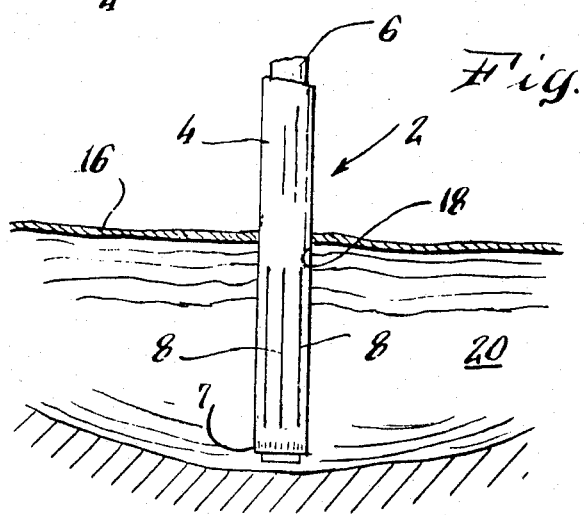
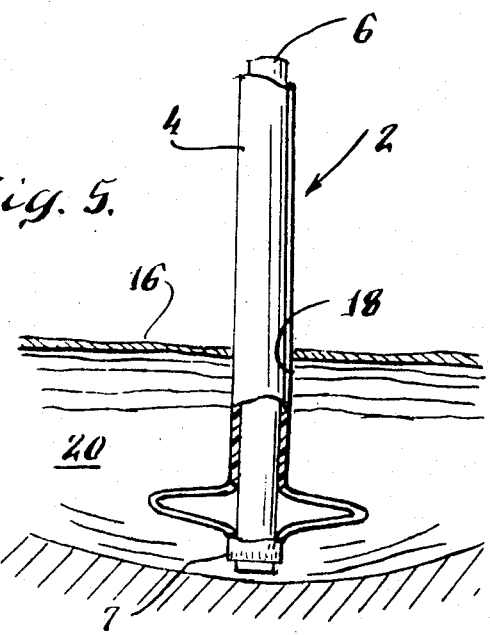
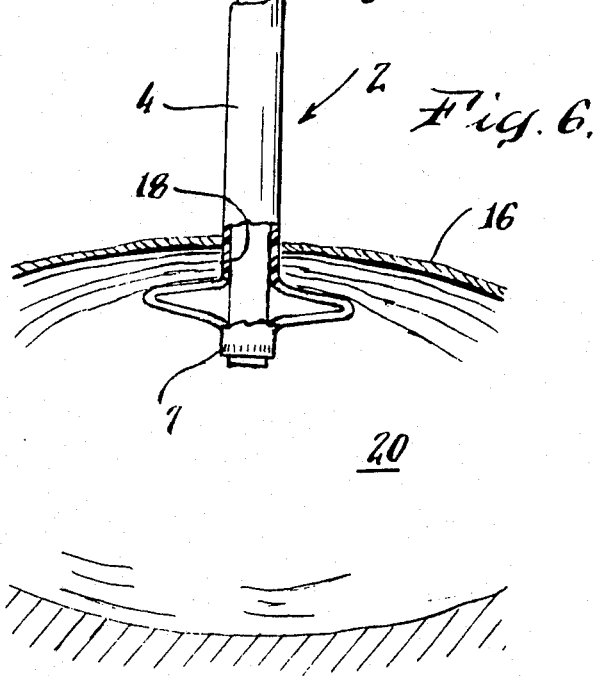

– 4,608,965 –

ENDOSCOPE RETAINER AND TISSUE RETRACTING DEVICE

TECHNICAL FIELD

This invention relates to an attachment for an endoscope for endoscopic surgery for retaining the endoscope within a body cavity and providing for retracting any soft tissue so that structures can be visualized more easily.

BACKGROUND ART

No similar device is known at this time.

DISCLOSURE OF INVENTION

An object of the present invention is to provide a device for a surgical endoscope which will not interfere in its insertion into an opening through the skin into a body cavity, yet provide enlargement within the cavity to prevent the endoscope from slipping out of the cavity and also providing for retracting soft tissue around the opening in the cavity away from the cavity to provide a better view therein.

Another object of the present invention is to provide a plastic tubular sleeve for an endoscope extending inwardly from its end which has multiple longitudinal slits near its tip. The inner dimension of the end of the tube has a friction fit over the endoscope for holding it in place, and the rearward portion of the tubular sleeve is moved forwardly, sliding over the endoscope with the slits opening up, providing radial extensions; a holding screw extends through the tubular sleeve and can be tightened against the endoscope to hold the sleeve in that position.

A further object of the present invention is to provide a method of operating in a body cavity which will prevent inadvertent endoscope removal and permit enlargement of the cavity by moving the expanded tip on the probe outwardly.

BRIEF DESCRIPTION OF THE DRAWINGS

FIG. 1 shows a tubular endoscope retaining and tissue retracting device mounted on the end of an endoscope;

FIG. 2 shows a tubular endoscope retaining and tissue retracting device with its end expanded to provide the retaining and retracting function;

FIG. 3 is an end view of the retaining and retracting device showing it expanded;

FIG. 4 is a view showing an endoscope having a tubular endoscope retaining and tissue retracting device mounted thereon, projecting through an opening in the skin of a body into a body cavity;

FIG. 5 is a view similar to FIG. 4 showing the retaining and retracting device expanded within the body cavity;

FIG. 6 is a view similar to FIG. 5, showing the endoscope and the retaining and retracting device moved outwardly from the bottom of the body cavity, pulling soft tissue or fatty material upwardly, enlarging the cavity.

BEST MODE FOR CARRYING OUT THE INVENTION

An endoscope retainer and tissue retracting device 2 according to the present invention is shown in FIGS. 1 and 2. The endoscope retainer and tissue retracting device 2 comprises a soft plastic cylindrical tube 4 with one end 7 being formed having a smaller end diameter. The portion of the soft plastic cylindrical tube 4 adjacent the end 7 having the smaller diameter is formed having longitudinal slits 8 forming flexible strips therebetween.

The other end of the endoscope retainer and tissue retracting device 2 has an enlarged portion 10 fixed thereto, having an internally threaded radial opening 12 therein for receiving a set screw 14. While a two-part construction is shown, the soft plastic cylindrical tube 4 and enlarged portion 10 can be made integral.

Prior to endoscopic surgery involving a small body cavity and soft tissue, the endoscope retainer and tissue retracting device 2 can be slipped over the probe portion of the endoscope 6 with the enlarged portion 10 going on first; the endoscope retainer and tissue retracting device 2 has sliding engagement with the probe portion of the endoscope 6 for most of its length until the end 7 of the soft plastic cylindrical tube 4 is reached. At this point, the reduced diameter of the end 7 is forced over the probe portion of the endoscope 6, providing a friction holding fit.

It can now be seen that as the enlarged portion 10 is moved along the probe portion of the endoscope 6, the flexible strips of soft plastic between the slits 8 will be forced outwardly as shown in FIGS. 2 and 3. When the strips are positioned outwardly, the set screw 14 is tightened to fix the position of the strips.

Any plastic having this ability to bend can be used. Nylon was used in one device made. If a slightly more rigid plastic is desired, the cylindrical tube 4 can be scored around the inner surface at location A and scored around the outer surface at the locations B and C, where the ends of the slits are.

Further, in the construction of an endoscope retainer and tissue retracting device 2, the device was approximately 3⅝ inches long (9.21 cm), while the slits 8 were ¾ inches long (1.9 cm), and positioned about 2/16 inches (0.32 cm) from the end 7.

In operation, the endoscope retainer and tissue retracting device 2 is placed over the probe portion of the endoscope 6, as set forth above, with the end 7 having a friction holding fit on the end of the probe portion. The endoscope 6 and endoscope retainer and tissue retracting device 2 is inserted through the skin 16 into a prepared opening 18 in the body into a body cavity 20, as shown in FIG. 4. The endoscope retainer and tissue retracting device 2 is moved forwardly by the surgeon to expand the strips formed by the slits 8, as shown in FIG. 5. If the body cavity 20 is not deep enough to permit proper opening of the strips, a solution, such as saline, can be forced into the body cavity 20 to expand the cavity 20 a little to receive the expanded strips. For example, this can be done in the area of knee surgery where a body cavity could be very small. The endoscope retainer and tissue retracting device 2 can be fixed in place on the probe portion of the endoscope 6 by tightening the set screw 14. Now the endoscope can be moved by the surgeon to position it in the cavity 20 to properly view the area to be operated on without fear of the endoscope 6 retracting from the body. Further, if soft tissue, or fat, prevents proper viewing, the endoscope retainer and tissue retracting device 2 and endoscope 6 can be withdrawn to pull the soft tissue back, enlarging the body cavity 20, permitting a line of sight to an operating area.

I claim:

1. An endoscope retainer and tissue retracting device including a soft plastic cylindrical tube for slidably mounting on the probe portion of an endoscope, the end of the soft plastic cylindrical tube having a slightly reduced diameter to have a friction holding fit over the end of an endoscope, a plurality of slits located around the soft plastic cylindrical tube adjacent the end of reduced diameter, said slits forming a plurality of flexible strips which bend to extend radially outwardly when their ends are brought together by sliding the other end of the soft plastic cylindrical tube along on the probe portion of an endoscope towards the end having a friction holding fit over the end of an endoscope, means for fixing the other end of the soft plastic cylindrical tube to an endoscope with the strips extending radially outwardly.

2. An endoscope retainer and tissue retracting device as set forth in claim 1 including at least four (4) slits.

3. An endoscope retainer and tissue retracting device as set forth in claim 1 wherein said means for fixing the other end of the soft plastic cylindrical tube is an enlarged sleeve with a set screw therein.

4. In combination, an endoscope, said endoscope having a cylindrical probe, a soft plastic cylindrical tube slidably mounted over said cylindrical probe, said soft plastic cylindrical tube having a slightly reduced diameter at one end providing a friction holding fit adjacent the end of said cylindrical probe, said soft plastic cylindrical tube having a plurality of slits located therearound adjacent the slightly reduced diameter, said slits forming a plurality of flexible strips which bend radially outwardly when the other end of said soft plastic cylindrical tube is slidably moved towards the end having the friction holding fit, means for fixing the other end of the soft plastic cylindrical tube to said endoscope to fix the strips in their bent position.

5. A method of viewing an internal body cavity with an endoscope including the steps of:
   (1) placing an expandable tip on the probe of the endoscope,
   (2) preparing a body opening into a body cavity;
   (3) inserting the endoscope and expandable tip through said opening into a body cavity; and
   (4) expanding said tip to prevent said probe of said endoscope from being accidentally withdrawn from said body opening and permit said expanded tip to draw soft body tissue outwardly to enlarge the body cavity to visualize body structures more easily.

6. In combination, an endoscope, said endoscope having a cylindrical probe, an endoscope retainer and tissue retracting device including a plastic cylindrical tube positioned on said cylindrical probe, said cylindrical tube having one end positioned adjacent the end of said cylindrical probe of said endoscope, means fixing said one end of said cylindrical tube directly to said cylindrical probe to prevent its removal from said cylindrical probe, said cylindrical tube having a plurality of slits located therearound adjacent its one end, said cylindrical tube having a rearward portion slidably mounted against said cylindrical probe, a plurality of flexible strips being formed by said slits, said strips being bent to extend radially outwardly when their ends are brought together, means for sliding the rearward portion of the plastic cylindrical tube on the cylindrical probe of said endoscope towards the one end of said cylindrical tube fixed to said cylindrical probe to bend said strips to extend radially outwardly, said radially extending strips retaining said endoscope in an operating cavity and providing for tissue retraction when said strips are fixed in their bent position, means for fixing the rearward portion of said cylindrical plastic tube to said endoscope to fix the strips in their bent position extending radially outwardly.

7. A combination as set forth in claim 6 wherein said cylindrical tube is approximately 9.21 cm in length, said slits are approximately 1.9 cm in length, and said slits are positioned about 0.32 cm from the one end of said cylindrical tube.

8. A combination as set forth in claim 6 wherein said cylindrical tube is of a length to extend externally of an operating cavity for direct slidable movement by a surgeon.

9. A combination as set forth in claim 6 wherein said means for fixing the rearward portion of said cylindrical plastic tube to said endoscope is a set screw in a threaded opening in the rearward portion of said cylindrical plastic tube.

10. A combination as set forth in claim 6 wherein said means fixing said one end of said cylindrical tube directly to said cylindrical probe is a friction fit, said one end of said cylindrical tube having a reduced diameter so that it has a friction holding fit when forced over the cylindrical probe.

* * * * *